United States Patent [19]

Folest et al.

[11] Patent Number: 4,758,315

[45] Date of Patent: Jul. 19, 1988

[54] PROCESS FOR THE ELECTROSYNTHESIS OF TERTIARY ARYLALKYLPHOSPHINES

[75] Inventors: Jean-Claude Folest, Creteil; Jacques Perichon, Sur Orge, both of France

[73] Assignee: Societe Nationale des Poudres et Explosifs, Paris, France

[21] Appl. No.: 117,822

[22] Filed: Nov. 9, 1987

[30] Foreign Application Priority Data

Nov. 10, 1986 [FR] France ................ 86 15630

[51] Int. Cl.$^4$ ................................................ C25C 1/00
[52] U.S. Cl. ................................................... 204/59 R
[58] Field of Search ...................................... 204/59 R

[56] References Cited

U.S. PATENT DOCUMENTS 4,655,883  4/1987  Farnung ............................ 204/59 R
4,689,123  8/1987  Noding .............................. 204/59 R

*Primary Examiner*—R. L. Andrews
*Attorney, Agent, or Firm*—Burns, Doane, Swecker & Mathis

[57] ABSTRACT

The process according to the invention is a process for the electrosynthesis of teritary arylalkylphosphines by electrochemical reduction of arylhalophosphines in the presence of aliphatic halides, in an organic solvent medium.

The anode, made of a reducing metal such as zinc, aluminum or magnesium, is sacrificed during the electrosynthesis.

The cell is preferably non-compartmented.

The process is simple and inexpensive.

Teritary arylalkylphosphines are compounds which are widely used in homogeneous catalytic systems.

15 Claims, No Drawings

PROCESS FOR THE ELECTROSYNTHESIS OF TERTIARY ARYLALKYLPHOSPHINES

The invention relates to a process for the electrosynthesis of tertiary arylalkylphosphines by electrochemical reduction of arylhalophosphines in the presence of aliphatic organic halides, the process being carried out in an electrolytic cell in an organic solvent medium containing a supporting electrolyte.

Tertiary phosphines, and in particular asymmetric tertiary phosphines, are products which are increasing in use on account of the rapid rise in their application in homogeneous catalysis.

At present, the main limitation to their development is their high cost, chiefly due to the complexity of their synthesis.

The principal known access routes to tertiary arylalkylphosphines are as follows:

reaction of an organometallic compound with a chlorophosphine, for example

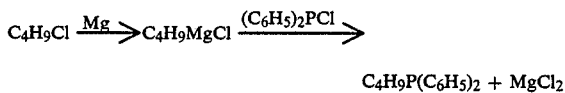

$$C_4H_9P(C_6H_5)_2 + MgCl_2$$

The disadvantages of this synthesis are those of organometallic compounds, namely, difficulty in preparing the reagent, use of finely divided reducing metals, unavoidable use of highly inflammable solvents (ethers, tetrahydrofuran), and poor or zero yields with halogenated derivatives bearing functional groups, such as $ClCH_2$—$COOC_2H_5$, $C_6H_5CH_2Cl$ or $CH_3COCH_2Cl$.

alkylation of the anion of a disubstituted phosphine with an aliphatic organic halide, for example:

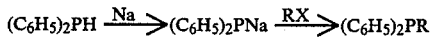

The main difficulty in this synthesis is linked to the stage of preparation of the phosphine anion, generally carried out using reducing metals.

Furthermore, as regards the electrochemistry of arylhalophosphines, the following reactions are known: R. E. DESSY et al., J.A.C.S., 88 (3), 467–70, 1966, carried out the electrochemical reduction of $(C_6H_5)_2PCl$ and obtained $(C_6H_5)_2P$—$P(C_6H_5)_2$. By a subsequent reaction with $C_2H_5Br$, they obtained $C_6H_5(C_2H_5)P$—$P$—$(C_2H_5)C_6H_5$.

Consequently, as far as the Applicant Company is aware, there is no simple and inexpensive process for the synthesis of tertiary arylalkylphosphines.

The subject of the present invention is such a process.

The process according to the invention for the synthesis of tertiary arylalkylphosphines is characterized in that the electrochemical reduction of arylhalophosphines is carried out in the presence of aliphatic organic halides in an electrolytic cell equipped with electrodes in an organic solvent medium containing a supporting electrolyte, and in that a sacrificial anode, made of a metal chosen from the group consisting of reducing metals and their alloys, is used. "Their alloys" is understood to mean any alloy containing at least one reducing metal.

"Aliphatic organic halide" is understood to mean an organic halide in which the halogen is not directly linked to a carbon atom of an aromatic ring.

Preferably, a sacrificial anode made of a metal chosen from the group consisting of zinc, aluminium, magnesium and their alloys is used.

"Their alloys" is understood to mean any alloy containing at least one of the abovementioned three metals, namely, zinc, aluminium or magnesium.

This process is very simple to perform, since it can be carried out in a single-compartment electrolytic cell without a diaphragm or a sintered membrane, which is very important, in particular at the industrial level.

This process can be performed with solvents of relatively low toxicity and low flammability, which are usable and used commonly in industry (N,N-dimethylformamide -DMF- for example).

It should also be noted that, according to the invention, there is an absence of degradation of the solvent at the anode, which is especially useful and advantageous.

Furthermore, compared with the processes known at present, the process according to the invention has the advantage of avoiding all the problems linked to the use of dangerous organometallic reagents: use of finely divided metals, of strongly reducing or highly basic reagents, and of dangerous solvents. It also has the advantage of permitting, unexpectedly, good yields to be obtained with aliphatic organic halides bearing functional groups, such as $ClCH_2$—$COOC_2H_5$, $C_6H_5CH_2Cl$ or $CH_3COCH_2Cl$.

The arylhalophosphines used in the process according to the invention correspond to the general formula $$A_n A'_{n'} P X_m$$

in which

X denotes a halogen preferably chosen from the group consisting of chlorine and bromine A and A' denote identical or different aromatic groups n, n' and m are integers such that $m+n+n'=3$, $m \neq 0$ and $n + n' \neq 0$.

Preferably, A and/or A' denote a phenyl group, which is optionally substituted.

It is especially preferable that the arylhalophosphine is diphenylchlorophosphine or phenyldichlorophosphine.

The aliphatic organic halides used in the process according to the invention correspond to the general formula RX' in which X' denotes a halogen preferably chosen from the group consisting of chlorine and bromine R denotes an aliphatic chain which is optionally substituted.

Preferably, R denotes an alkyl chain, optionally substituted, containing from 1 to 18 carbon atoms.

It is especially preferable that R denotes an alkyl chain, optionally substituted, containing from 1 to 8 carbon atoms.

When R denotes a substituted chain, the substituents must be more difficult to reduce, under the conditions of the electrosynthesis, than the arylhalophosphine. These substituents are preferably chosen from the group consisting of alkyl chains containing from 1 to 8 carbon atoms, ester groups, halogens, aryl groups and vinyl groups.

According to an especially preferred variant of the invention, R denotes an alkyl chain substituted with a halogen, which makes it possible to obtain, for example, diphosphines of general formula

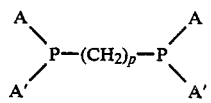

A and A' having the meaning stated above and p being an integer equal to or greater than 2, by reduction of AA'PCl in the presence of Cl—(CH$_2$)p—Cl.

The electrolytic cell is a conventional cell, preferably non-compartmented. This possibility of using a single-compartment cell is a major advantage, as has already been mentioned.

According to the process which is the subject of the invention, the anode is sacrificed during the electrochemical reaction, the anode being the seat thereof. A sacrificial anode made of a metal chosen from the group consisting of reducing metals and their alloys, preferably from the group consisting of magnesium, zinc, aluminium and their alloys, is used.

This anode may be of any form, and in particular all the conventional forms for metal electrodes such as, for example, twisted wire, flat bar, cylindrical bar, renewable bed, beads, gauze or grid.

Preferably, a cylindrical bar whose diameter is suited to the dimensions of the cell is used.

The cathode is any metal such as stainless steel, nickel, platinum, gold or silver, or is of carbon. It preferably consists of a cylindrical grid or plate arranged concentrically around the anode.

The electrodes are supplied with direct current via a stabilized supply.

The organic solvents used in the context of the present invention are the solvents that are only slightly protic which are commonly used in organic electrochemistry. There may be mentioned, for example, DMF, acetonitrile, tetramethylurea (TMU), N-methylpyrrolidone (NMP), hexamethylphosphorotriamide (HMPT) and the mixtures of these products.

The supporting electrolytes used are those which are customarily used in organic electrochemistry. There may be mentioned, for example, the salts in which the anion is a halide, a perchlorate or a fluoroborate and the cation a quaternary ammonium, lithium, sodium, potassium, magnesium, zinc or aluminium.

Tetrabutylammonium iodide or fluoroborate is preferably used.

Preferably, the concentration of supporting electrolyte in the organic solvent is between 0.01M and 0.5M.

Preferably also, the concentration of arylhalophosphine in the organic solvent is between 0.2M and 2M.

The ratio between the concentrations in the organic solvent of the aliphatic organic halide and the arylhalophosphine can assume any value. Preferably, an excess of aliphatic organic halide is used, and in particular a ratio of concentrations of between 1.5 and 3.

The reaction temperature is generally between −10° C. and +50° C., and preferably between 0° and +10° C.

The current density on the cathode is preferably chosen between 0.5 and 10 A/dm$^2$. The reaction is generally performed at constant intensity, but it is also possible to work at constant voltage, at a controlled potential or with variable intensity and potential.

Before the electrolysis, the solution is deoxygenated by bubbling an inert gas, for example nitrogen or argon, through it.

The invention is illustrated by the non-limiting examples which follow. To carry out these examples, a non-compartmented conventional electrolytic cell is used.

The upper part of the cell is made of glass and is equipped with 5 necks permitting the inflow and outflow of the inert gas, the possible withdrawal of samples of solution during electrolysis, and the passage of the electrical conductors.

The lower part consists of a cap equipped with a seal, screwed onto the upper glass part.

The total volume of the cell is 45 cm$^3$.

The anode is composed of a cylindrical bar 1 cm in diameter.

It is introduced into the cell through the central neck and is thus situated approximately in an axial position with respect to the cell. It is immersed in the solution over a length of approximately 2.5 cm.

The cathode consists of a cylindrical gauze arranged concentrically around the anode. The working surface of the cathode is of the order of 20 cm$^2$. The cell is immersed in a thermostatic bath adjusted to the chosen temperature.

A solution of 20 mmol of monohaloarylphosphine (or 10 mmol of dihaloarylphosphine) and N mmol of aliphatic organic halide in 30 ml of solvent, rendered electrically conductive by adding 1.5 mmol of tetrabutylammonium iodide, is introduced into the cell.

After the solution is outgassed by bubbling nitrogen through it, a current of constant intensity 0.4 A is applied between the electrodes for approximately 3 h, which corresponds to the complete disappearance of the arylhalophosphine.

After the electrolysis, two methods of extraction have been employed, according to the phosphine obtained:

Method A: acidification of the reaction medium with an aqueous solution of hydrochloric acid followed by extraction of the synthesized phosphine with diethyl ether.

Method B: acidification of the solution to pH 4–5 with a cold dilute aqueous solution of hydrochloric acid followed by filtration and recrystallization of the collected precipitate in butanol.

The products obtained are identified according to the traditional methods of identification, by comparison with authentic samples. The following methods were employed in particular: mass spectrometry, gas chromatography, polarography in the presence of nickel salts, measurement of the melting point.

EXAMPLES 1 to 19

The following table specifies for each example, on the one hand the particular working conditions, namely the nature of the starting arylhalophosphine, the nature and quantity of the starting aliphatic organic halide, the nature of the solvent and of the electrodes used, and the method of extraction employed, and on the other hand the result obtained, that is to say the nature of the product synthesized and the corresponding yield of isolated product, expressed with respect to the starting arylhalophosphine.

TABLE

| Ex. No | Starting arylhalo- phosphine | Starting aliphatic organic halide (mmol) | Solvent | Cathode | Anode | Method of extraction | Product obtained | Yield % |
|---|---|---|---|---|---|---|---|---|
| 1 | $\phi_2$PCl | nBuBr (30) | DMF | SS | Mg | A | $\phi_2$PBu | 82 |
| 2 | $\phi_2$PCl | nBuBr (30) | NMP | SS | Mg | A | $\phi_2$PBu | 93 |
| 3 | $\phi_2$PCl | $\phi$CH$_2$Cl (30) | NMP | SS | Mg | A | $\phi_2$PCH$_2\phi$ | 44 |
| 4 | $\phi_2$PCl | $\phi$CH$_2$Cl (30) | DMF | SS | Mg | A | $\phi_2$PCH$_2\phi$ | 30 |
| 5 | $\phi_2$PCl | ClCH$_2$CO$_2$Et (30) | DMF | SS | Mg | A | $\phi_2$PCH$_2$CO$_2$Et | 45 |
| 6 | $\phi_2$PCl | ClCH$_2$CO$_2$Et (30) | NMP | SS | Mg | A | $\phi_2$PCH$_2$CO$_2$Et | 53 |
| 7 | $\phi_2$PCl | ClCH$_2$CO$_2$Et (30) | DMF | Pt | Mg | A | $\phi_2$PCH$_2$CO$_2$Et | 70 |
| 8 | $\phi_2$PCl | ClCH$_2$CO$_2$Et (30) | DMF | C | Zn | A | $\phi_2$PCH$_2$CO$_2$Et | 30 |
| 9 | $\phi_2$PCl | BrCH$_2$CO$_2$Et (30) | DMF | SS | Mg | A | $\phi_2$PCH$_2$CO$_2$Et | 10 |
| 10 | $\phi_2$PCl | CH$_3$CHClCO$_2$Et (30) | DMF | SS | Mg | A | $\phi_2$PCH(CH$_3$)CO$_2$Et | 45 |
| 11 | $\phi_2$PCl | $\phi$CH=CHCH$_2$Cl (30) | DMF | SS | Mg | A | $\phi_2$PCH$_2$CH=CH$\phi$ | 15 |
| 12 | $\phi_2$PCl | Br(CH$_2$)$_4$Br (10) | NMP | SS | Mg | B | $\phi_2$P(CH$_2$)$_4$P$\phi_2$ | 83 |
| 13 | $\phi_2$PCl | Br(CH$_2$)$_4$Br (10) | DMF | SS | Mg | B | $\phi_2$P(CH$_2$)$_4$P$\phi_2$ | 60 |
| 14 | $\phi_2$PCl | Br(CH$_2$)$_2$Br (10) | NMP | SS | Mg | B | $\phi_2$P(CH$_2$)$_2$P$\phi_2$ | 42 |
| 15 | $\phi_2$PCl | ClCH$_2$CH$_2$Cl (10) | NMP | SS | Mg | B | $\phi_2$P(CH$_2$)$_2$P$\phi_2$ | 67 |
| 16 | $\phi$PCl$_2$ | nBuBr (30) | DMF | SS | Mg | A | $\phi$PBu$_2$ | 55 |
| 17 | $\phi$PCl$_2$ | CH$_3$(CH$_2$)$_6$Br (30) | DMF | SS | Mg | A | $\phi$[(CH$_2$)$_6$CH$_3$]$_2$ | 39 |
| 18 | $\phi$PCl$_2$ | ClCH$_2$CO$_2$Et (30) | DMF | SS | Mg | A | $\phi$P(CH$_2$CO$_2$Et)$_2$ | 19 |
| 19 | $\phi$PCl$_2$ | $\phi$CH$_2$Br (30) | DMF | SS | Mg | A | $\phi$P(CH$_2\phi$)$_2$ | 17 |

SS means stainless steel
$\phi$ means C$_6$H$_5$
Et means C$_2$H$_5$
Bu means C$_4$H$_9$

We claim:

1. Process for the synthesis of tertiary arylalkylphosphines, characterized in that the electrochemical reduction of arylhalophosphines is carried out in the presence of aliphatic organic halides in an electrolytic cell equipped with electrodes in an organic solvent medium containing a supporting electrolyte, and in that a sacrificial anode, made of a metal chosen from the group consisting of reducing metals and their alloys, is used.

2. Synthesis process according to claim 1, characterized in that a sacrificial anode made of a metal chosen from the group consisting of zinc, magnesium, aluminium and their alloys is used.

3. Process according to claim 1, characterized in that the arylhalophosphines correspond to the general formula $A_nA'_{n'}PX_m$ in which X denotes a halogen preferably chosen from the group consisting of chlorine and bromine A and A' denote identical or different aromatic groups n, n' and m are integers such that $m+n+n'=3$, $m \neq 0$ and $n+n' \neq 0$.

4. Process according to claim 3, characterized in that X denotes chlorine.

5. Process according to claim 3, characterized in that A and/or A' denote a phenyl group which is optionally substituted.

6. Process according to either of claim 4, characterized in that the arylhalophosphine is diphenylchlorophosphine or phenyldichlorophosphine.

7. Process according to claim 1, characterized in that the aliphatic organic halides correspond to the general formula RX' in which X' denotes a halogen preferably chosen from the group consisting of chlorine and bromine R denotes an aliphatic chain which is optionally substituted.

8. Process according to claim 7, characterized in that R denotes an alkyl chain, optionally substituted, containing from 1 to 18 carbon atoms.

9. Process according to either of claim 7, characterized in that R is substituted with a substituent chosen from the group consisting of alkyl chains containing from 1 to 8 carbon atoms, ester groups, halogens, aryl groups and vinyl groups.

10. Process according to either of claim 8, characterized in that R denotes an alkyl chain substituted with a halogen.

11. Process according to either of claim 1, characterized in that the electrolytic cell is non-compartmented.

12. Process according to claim 1, characterized in that the organic solvent is chosen from the group consisting of N,N-dimethylformamide, tetramethylurea, tetrahydrofuran, N-methylpyrrolidone, hexamethylphosphorotriamide and the mixtures of these products.

13. Process according to claim 1, characterized in that the supporting electrolyte is tetrabutylammonium iodide or fluoroborate.

14. Process according to claim 1, characterized in that the reaction temperature is between $-10°$ C. and $+50°$ C.

15. Process according to claim 1, characterized in that the mole ratio aliphatic organic halide/arylhalophosphine is between 1.5 and 3.

* * * * *